United States Patent [19]

Barlow et al.

[11] Patent Number: 4,536,530

[45] Date of Patent: Aug. 20, 1985

[54] WATER TREE RESISTANT COMPOUNDS AND POLYMER COMPOSITIONS CONTAINING THE SAME

[75] Inventors: Anthony Barlow; Melvin F. Maringer, both of Cincinnati, Ohio

[73] Assignee: National Distillers and Chemical Corporation, New York, N.Y.

[21] Appl. No.: 575,974

[22] Filed: Feb. 1, 1984

[51] Int. Cl.³ .......................... C08K 5/51; C08K 5/52
[52] U.S. Cl. .................................. 524/109; 524/82; 524/93; 524/103; 524/110; 524/137; 524/138; 524/140; 174/110 SR; 174/110 PM; 174/110 AR; 174/110 V; 174/110 SY; 174/110 N
[58] Field of Search ............ 524/DIG. 912, 109, 110, 524/137, 138, 140, 82, 99, 103; 174/110 SR, 110 PM, 110 AR, 110 V, 110 SY, 110 N; 525/40, 41

[56] References Cited

U.S. PATENT DOCUMENTS

| | | | |
|---|---|---|---|
| 2,493,390 | 1/1950 | Chaban | 524/140 |
| 3,219,615 | 11/1965 | Phillips | 524/109 |
| 3,404,121 | 10/1968 | Barkey | 524/140 |
| 4,219,607 | 8/1980 | Cammack et al. | 174/110 SR |
| 4,233,470 | 11/1980 | Wight | 524/303 |

FOREIGN PATENT DOCUMENTS 49-32311  8/1974  Japan .

Primary Examiner—Veronica P. Hoke
Attorney, Agent, or Firm—Kenneth D. Tremain

[57] ABSTRACT

Organophosphorus compounds having the general formula

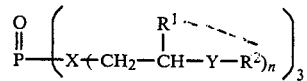

useful as water tree resistant additives for polymeric compositions.

20 Claims, No Drawings

WATER TREE RESISTANT COMPOUNDS AND POLYMER COMPOSITIONS CONTAINING THE SAME

BACKGROUND OF THE INVENTION

This invention relates to polymeric compositions containing organophosphorous compounds, such as substituted phosphates, having increased resistance to water treeing, said compositions being useful as insulation for electrical cables.

Polymeric compositions are well-known and are used extensively as insulation materials for wire and cable. As an insulator, it is important that the composition have various physical and electrical properties, such as resistance to mechanical cut through, stress crack resistance and dielectric failure. Recent publications have indicated that water tree growth and electrical tree growth in the insulation are particularly important problems since they are associated with, though not necessarily totally responsible for, dielectric failure.

An important application for an insulation material is in high voltage transmission and distribution cable, especially in direct buried underground service and three types of trees have been observed in power cables, to wit, electrical trees, water trees and electrochemical trees. It is generally believed that electrical trees are generated by corona discharges causing fusion and breakdown of the polymer, whereas water trees are usually observed in cables buried in wet locations and have a different appearance compared to the electrical trees. The electrochemical trees are similar to the water trees but are characterized by the presence of metal ions in the trees.

U.S. Pat. No. 4,144,202 granted to Ashcraft et al. relates to inhibiting the electrical breakdown of insulation by water treeing in dielectric materials based on ethylene polymers. This patent discusses electrical failures which are due to treeing and explains the concept of treeing and some of the causes for treeing. In general, as the polymeric composition breaks down the damage progresses through the insulator or dielectric, in a path that looks something like a tree. Treeing usually is a slow type failure and may take years to cause a failure in the insulation. As disclosed in the patent, water treeing is inhibited in the ethylene polymer compositions by employing therein certain organo silane compounds. In particular, the organo silane is a silane containing an epoxy containing radical. Suitable polymers, adjuvants and processing procedures for preparing the composition are described in the patent, which patent is hereby incorporated by reference.

U.S. Pat. No. 4,206,260 granted to McMahon relates to insulation particularly suitable for high voltage cable containing an effective amount of an alcohol of 6 to 24 carbon atoms which imparts electrical tree growth resistance to the composition. This patent, as in U.S. Pat. No. 4,144,202, supra, contains a discussion of the electrical treeing problem in polymer compositions and cites numerous patents attempting to overcome this problem. Suitable polymers, adjuvants and preparation procedures are noted therein and this patent is hereby incorporated by reference.

German Offenlegungsschrift No. 2,737,430 discloses that certain alkoxysilanes added to polyolefin insulation prevent water-tree formation. Several trimethoxy and triethoxy silanes are said to be useful.

U.S. Pat. No. 3,553,348 granted to Betts, British Pat. No. 1,248,256 granted to General Electric Company and British Pat. No. 1,277,378 granted to General Electric Company relate to mineral filled polymer compositions useful as electrical wire and cable insulation. The mineral filler is treated with an organosilane such as an alkyl alkoxysilane or a vinyl alkoxysilane to decrease the porosity of the composition.

SUMMARY OF THE INVENTION

It is one object of the present invention to provide organophosphorus compounds, such as substituted phosphates, particularly useful as water tree retardance additives.

Another object of this invention is to provide polymeric compositions containing said organophosphorus compounds, such as substituted phosphates, which exhibit enhanced resistance to water treeing.

These and other objects are accomplished herein by providing polymeric compositions containing effective anti-treeing amounts of phosphates and other organophosphorus compounds having the general formula:

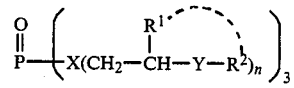

wherein X is selected from the group consisting of O, S, N and $NR^3$, Y is selected from the group consisting of O, S, and $NR^3$, $R^1$ and $R^2$ are independently selected from the group consisting of hydrogen, alkyl, cycloalkyl, alkenyl, cycloalkenyl and phenyl, $R^3$ is hydrogen or alkyl of from 1 to 6 carbon atoms, and wherein $R^1$ and $R^2$ may be taken with the carbon atom and Y substituent to which they are respectively bonded to form a ring and with the proviso that when X is O, S or $NR^3$, n is 1, and when X is N, n is 2.

DETAILED DESCRIPTION OF THE INVENTION

The organophosphorus compounds utilized herein as water tree resistant additives are generally known compounds. These compounds having the general structure:

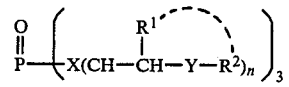

wherein X, Y, $R^1$, $R^2$ and n are as defined before, are either commercially available or can be readily synthesized by known procedures. For example, typically, phosphates are prepared by reacting phosphorus oxychloride with an alcohol, such as glycol ether, in the presence of a hydrogen halide acceptor, such as pyridine, methylalanine, or the like. The phosphorothioates may be prepared by reacting phosphorus oxychloride with a mercaptan while the phosphoricamides may be prepared by reacting an amine with phosphorus oxychloride.

Typical phosphates and other organophosphorus compounds contemplated herein as water-tree additives and within the above general formula include tris(2-ethoxyethyl)phosphate($O=P(OCH_2CH_2OCH_2CH_3)_3$), tris(2-propoxyethyl)phosphate($O=P(OCH_2CH_2OCH_2CH_2CH_3)_3$), tris(2-butoxyethyl)phosphate(O=P(OCH$_2$CH$_2$OCH$_2$CH$_2$CH$_2$CH$_3$)$_3$), tris(2-phenoxyethyl)phosphate

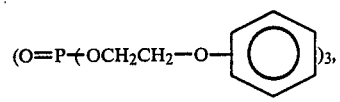

tris(2-acetoxyethyl)phosphate

tris[2-(2-chloroethoxy)ethyl]phosphate(O=P(OCH$_2$CH$_2$OCH$_2$CH$_2$Cl)$_3$), tris(tetrahydrofurfuryl)phosphate

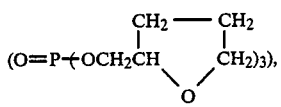

tris(2-aminoethyl)phosphate(O=P(OCH$_2$CH$_2$NH$_2$)$_3$), tris(2-ethylaminoethyl)phosphate(O=P-(OCH$_2$CH$_2$NHCH$_2$CH$_3$)$_3$), tris(2-diethylaminoethyl)phosphate(O=P(OCH$_2$CH$_2$N(CH$_2$CH$_3$)$_2$]$_3$), tris(2-hydroxyethyl)phosphate(O—P(OCH$_2$CH$_2$OH)$_3$), tris(2-mercaptoethyl)phosphate(O=P-(OCH$_2$CH$_2$SH)$_3$), tris(2-methylthioethyl)phosphate(O=P(OCH$_2$CH$_2$SCH$_3$)$_3$), tris(2-ethoxyethyl)phosphorotrithioate(O=P(SCH$_2$CH$_2$OCH$_2$CH$_3$)$_3$), tris(2-phenoxyethyl)phosphorotrithioate

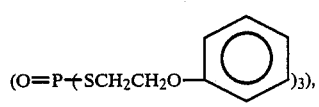

trifurfuryl phosphorotrithioate

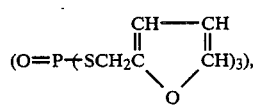

tris(2-mercaptoethyl)phosphorotrithioate(O=P-(S—CH$_2$CH$_2$SH)$_3$), tris(2-aminoethyl)phosphorotrithioate(O=P(SCH$_2$CH$_2$NH$_2$)$_3$), tris(2-hydroxyethyl)phosphorotrithioate(O=P(SCH$_2$CH$_2$OH)$_3$), N,N',N''-tris(2-ethoxyethyl)phosphorictriamide(O=P(NHCH$_2$CH$_2$OCH$_2$CH$_3$)$_3$), hexa(2-hydroxyethyl)phosphorictriamide(O=P[N(CH$_2$CH$_2$OH)$_2$]$_3$), hexa(2-ethoxyethyl)phosphorictriamide(O=P[N(CH$_2$CH$_2$OCH$_2$CH$_3$)$_2$]$_3$), hexa(2-tetrahydropyranylmethyl)phosphorictriamide

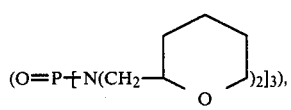

hexa(2-ethylthioethyl)phosphorictriamide O=P[N(CH$_2$CH$_2$SCH$_2$CH$_3$)$_2$]$_3$), hexa(2-mercaptoethyl)phosphorictriamide(O=P[N(CH$_2$CH$_2$SH)$_2$]$_3$), and the like.

In general, the polymers suitable for use in the practice of this invention include any normally solid synthetic organic polymeric thermoplastic resin. Included are polyolefins and copolymers thereof, vinyl, olefin-vinyl copolymers, olefin-allyl copolymers, polyamides, acrylics, polystyrenes, cellulosics, polyesters and fluorocarbons.

The polyolefins include normally solid polymers of olefins, particularly mono-alpha-olefins, which comprise from about two to about six carbon atoms, e.g., polyethylene, polypropylene, polybutene, polyisobutylene, poly(4-methyl-pentene), and the like. Preferred polyolefins are polyethylene and polypropylene. Polyethylene is especially preferred. Specific polyethylenes include linear low density polyethylene. An especially preferred polyethylene because of its demonstrated effectiveness is termed NA 310 and is sold by National Distillers and Chemical Company.

Copolymers of ethylene, and other compounds interpolymerizable with ethylene such as butene-1, pentene-1, styrene and the like may be employed. In general the copolymer will comprise about 50 weight % or more ethylene. Other copolymers, such as ethylene-propylene rubber (EPR) and ethylene-propylene-diene monomer (EPDM) are also contemplated herein.

Suitable vinyl polymers include polyvinyl chloride, polyvinyl acetate, vinyl chloride/vinyl acetate copolymers, polyvinyl alcohol and polyvinyl acetal.

Suitable olfein-vinyl copolymers include ethylene-vinyl acetate, ethylene-vinyl propionate, ethylene-vinyl isobutyrate, ethylene-vinyl alcohol, ethylene-methyl acrylate, ethylene-ethyl acrylate, ethylene-ethyl methacrylate, ethylene-acrolein, and the like. In general the ethylene constitutes at least about 25% of such copolymers by weight.

Olefin-allyl copolymers include ethylene-allyl benzene, ethylene-allyl ether, and the like.

When it is desired to use a polymeric composition which can be crosslinked, crosslinking can be accomplished by any of the known procedures such as chemical means including peroxide cross-linking; by radiation using electron accelerators, gamma-rays, high energy radiation, such as X-rays, microwaves etc.; or by thermal crosslinking. The basic procedures for crosslinking polymers are extremely well known to the art and need not be described here in detail.

Conventional crosslinking agents such as organic peroxides may be suitably employed. Typical organic peroxide free radical generators include dicumyl peroxide; 2,5-bis(tert.-butyl peroxy)-2,5-dimethylhexane; di-t-butylperoxide; benzoyl peroxide; α,α'bis(-butyl peroxy)diisopropyl benzene and the like, as discussed in U.S. Pat. No. 3,287,312. The amount of organic peroxide, when employed, will range from about 0.5 to 5.0% by weight based on the total weight of the composition, or about 0.5 to 10 phr, preferably 3 to 6 phr.

Minor amounts of other additives may also be employed in conventional amounts to obtain the desired results. Conventional antioxidants such as the hindered phenols, polyquinolines and the like may be employed. Other ingredients that may be included are plasticizers, dyes, pigments, heat and light stabilizers, antistatic agents and the like.

The compositions of this invention are generally unfilled polymer compositions. The term "unfilled" as applied to the instant composition shall mean a composition which contains less than 10% of a conventional polymer filler. For certain applications and to meet particular specifications the unfilled compositions herein may contain no filler. The compositions of this invention may contain, therefor, 0 to less than 10% filler. When polymers such as ethylene-propylene rubber (EPR) and ethylene-propylene-diene monomer (EPDM) are employed however, from about 20% to about 30% filler are generally used. Such compositions are also intended to be within the scope of this invention. Accordingly, fillers, such as mineral fillers, may be employed to this limited extent in preparing the compositions of this invention, but in the particularly preferred embodiment and for certain uses, these compositions contain no fillers.

The polymer compositions of this invention can be prepared by mixing the various ingredients. When the organic compound and the polymeric component are mixed together to form the instant compositions, the organic compound and polymer component are homogeneously dispersed in each other. The order of mixing and specific procedure employed are not critical except to the extent that from the time the peroxide is added, if employed, the temperature is less than about 130° C. in order to prevent premature curing of the composition. This precaution, however, is conventional in the art.

The components may be mixed on a variety of apparatus including multi-roll mills, screw mills, continuous mixers, compounding extruders and Banbury mixers.

Amounts of phosphate added to the polymeric composition for purposes herein include any effective water tree resistant amount. These amounts are generally in the range of from about 0.1% to about 5.0% based on the resin.

After being extruded onto wire or cable, or other substrate, the crosslinkable compositions are vulcanized at elevated temperatures, e.g., above about 180° C. using conventional vulcanizing procedures.

In order to determine the utility and effectiveness of the polymeric compositions of the present invention with regard to its inhibiting effect on the water treeing the compositions were evaluated by the use of accelerated tests.

The water tree test is performed using a procedure similar to that described in U.S. Pat. No. 4,144,202. A compression molded disc about 150 millimeters (mm.) in diameter having 10 conical depressions was prepared for each composition. The geometry of the disc and dimensions of the depressions are substantially the same as shown in U.S. Pat. No. 4,144,202. The base of the disc is sprayed with silver paint which serves as the ground electrode. An acrylic tube 6" long is clamped to the upper face forming a test cell. About 150 ml. of 0.01N sodium chloride solution was poured into the cell and the air bubbles trapped on the surface of the sample were removed. A platinum wire ring was then immersed in the electrolyte and connected to the electrical supply which provides 5 KV at a frequency of 3 KHz. Samples were energized for 22 hours after which time they were removed from the test cell and washed with distilled water. The ten depressions were cut from the disc and stained to make the water trees more visible. Thin sections were obtained with a microtome, which were then examined microscopically (at 200×) and the tree size measured. Normally four discs were made for each sample so that the average tree size is calculated from forty individual measurements. In evaluating different tree retardants, the relative tree size was determined by comparing the average tree size obtained on a standard thermoplastic high voltage insulation material containing no tree retardant additives.

Various embodiments of the present invention will now be illustrated by reference to the following specific examples. It is to be understood, however, that such examples are presented for purposes of illustration only, and the present invention is in no way to be deemed as limited thereby.

EXAMPLE 1

Tris(2-Ethoxyethyl)Phosphate

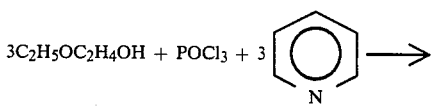

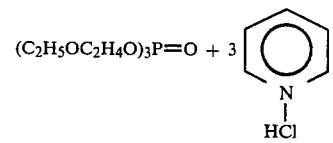

Into a 3-necked, 1000 ml round bottomed flask equipped with mechanical stirrer, thermometer, condenser, and dropping funnel were added 1.2 moles of ethyl cellosolve, 1.3 moles of dry pyridine and 400 ml of dry toluene. While stirring, the flask was cooled to +5° C. Slowly, from a dropping funnel was added 0.4 moles of phosphorous oxychloride in 100 ml of toluene while always maintaining the flask temperature below 15° C. After ½ hour, the flask was allowed to come to room temperature and held at that temperature for 3 hours.

The pyridine hydrochloride precipitate was dissolved in excess water and the toluene layer separated in a separatory funnel and dried over magnesium sulfate overnight. The toluene was then flashed off in a rotatory-vacuum apparatus, and the product distilled. B.P.: 158°–60° C. at 1 mmHg. Yield 64%.

EXAMPLE 2

Tris(2-Butoxyethyl)Phosphate

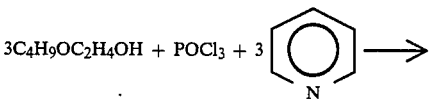

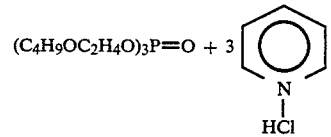

Into a 1-liter round bottom flask were placed 1.3 moles of dry pyridine, 1.2 moles of butoxyethanol and 100 ml of dry toluene. The solution was cooled to 5° C. and 0.4 mole of phosphorous oxychloride was slowly added from a dropping funnel while maintaining the reaction flask temperature below 10° C. After addition of the phosphorous oxychloride, the flask was heated to 80° C. and held at this temperature for 2 hours. The reaction mixture was then cooled to room temperature and 150 ml of water was added to dissolve the pyridine hydrochloride.

The toluene/butoxyethylphosphate was dried over magnesium sulfate and the toluene distilled at 50 mmHg. The tris(butoxyethyl)phosphate was then distilled under a vacuum of 2.2 mmHg. B.P. 212°–214° C.

EXAMPLE 3

The effectiveness of 1.5 wt.% tris(2-ethoxyethyl)-phosphate and 1.5 wt.% tris(2-butoxyethyl)phosphate used separately as a water tree retardant additive in polyethylene insulation (NA 310-06) results in the following test data:

|  | Boiling Point | Water Tree Size - μm |
|---|---|---|
| NA 310-06 |  | 210 |
| Tris(2-ethoxyethyl) phosphate $(C_2H_5OC_2H_4O)_3P=O$ | 158° C. at 1 mm | 87 |
| Tris(2-butoxyethyl) phosphate $(C_4H_9OC_2H_4O)_3P=O$ | 214° C. at 2.2 mm | 58 |

Obviously, other modifications and variations of the present invention are possible in the light of the above teachings. It is, therefore, to be understood that changes may be made in the particular embodiments of this invention as defined by the appended claims.

We claim:

1. A polymeric composition having enhanced resistance to water treeing and being devoid of anti-tracking additive and inorganic peroxide and comprising an intimate admixture of:
   a polymeric component and
   an effective water treeing inhibiting amount of about 0.1 to 5% by weight, based on the weight of said polymeric component, of, as the sole antitreeing agent, a compound having the general formula:

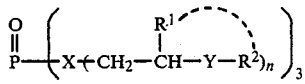

wherein X is selected from the group consisting of O, S, N and $NR^3$, Y is selected from the group consisting of O, S, and $NR^3$, $R^1$ and $R^2$ are independently selected from the group consisting of hydrogen, alkyl, cycloalkyl, alkenyl, cycloalkenyl, and phenyl, $R^3$ is hydrogen or alkyl of from 1 to 6 carbon atoms and wherein $R^1$ and $R^2$ may be taken with the carbon atom and Y substituent to which they are respectively bonded to form a ring, and
   with a first proviso that when X is O, S or $NR_3$, n is 1, and when X is N, n is 2, and
   with a second proviso that said polymeric component is other than a polyurethane, and
   with a third proviso that said composition contains about 20 to 30% by weight of filler when said polymeric component is ethylene-propylene rubber or ethylene-propylene-diene monomer copolymer and said composition contains 0 to less than 10% by weight of filler when said polymeric component is other than said rubber or said copolymer.

2. The polymeric composition of claim 1 wherein said phosphate is selected from the group consisting of tris-(ethoxyethyl)phosphate and tris(2-butoxyethyl)phosphate.

3. The polymeric composition of claim 1 wherein the polymeric component is polyethylene.

4. Electrical wire or cable insulated with the polymeric composition of claim 1.

5. Electrical wire or cable as in claim 4 insulated with an unfilled polymeric composition.

6. Electrical wire or cable as in claim 5 in which the polymeric component is polyethylene.

7. Electrical wire or cable as in claim 6 in which said compound is tris-(2-ethoxyethyl)phosphate.

8. Electrical wire or cable as in claim 6 in which said compound is tris-(2-butoxyethyl)phosphate.

9. Electrical wire or cable as in claim 4 in which the polymeric component is crosslinked.

10. A method of stabilizing a polymeric insulated electrical conductor against water treeing, said composition being devoid of anti-tracking additive, which comprises
    coating an electrical conductor with an insulating effective amount of a polymeric insulating composition, said composition comprising an intimate admixture of
    a polymeric component and
    an effective water treeing inhibitor amount of about 0.1 to 5% by weight, based on the weight of said polymeric component, of a compound having the general structure

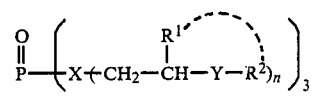

wherein X is selected from the group consisting of O, S, N and $NR^3$, Y is selected from the group consisting of O, S and $NR^3$, $R^1$ and $R^2$ are independently selected from the group consisting of hydrogen, alkyl, cycloalky, alkenyl, cycloalkenyl, and phenyl, $R^3$ is hydrogen or alkyl of from 1 to 6 carbon atoms and wherein $R^1$ and $R^2$ may be taken with the carbon atom and Y substituent to which they are respectively bonded to form a ring, and
    with a first proviso that when X is O, S or $NR_3$, n is 1, and when X is N, n is 2, and
    with a second proviso that said composition contains about 20 to 30% by weight of filler when said polymeric component is ethylene-propylene rubber or ethylene-propylene-diene monomer copolymer and said composition contains 0 to less than 10% by weight of filler when said polymeric component is other than said rubber or said copolymer.

11. The method of claim 4 wherein said phosphate is selected from the group consisting of tris(2-ethoxyethyl)phosphate and tris(2-butoxyethyl)phosphate.

12. The method of claim 5 wherein said polymeric component is polyethylene.

13. A polymeric composition having enhanced resistance to water treeing and being devoid of anti-tracking additive and inorganic peroxide and comprising an intimate admixture of
    a polymeric component and
    an effective water treeing inhibiting amount of about 0.1 to 5% by weight, based on the weight of said polymeric component, of, as the sole antitreeing agent, a compound selected from the group consisting of:
    tris(2-ethoxyethyl)phosphate
    tris(2-propoxyethyl)phosphate
    tris(2-butoxyethyl)phosphate
    tris(2-phenoxyethyl)phosphate tris(2-acetoxyethyl)phosphate
tris[2-(2-chloroethoxy)ethyl]phosphate
tris(tetrahydrofurfuryl)phosphate
tris(2-aminoethyl)phosphate
tris(2-ethylaminoethyl)phosphate
tris(2-diethylaminoethyl)phosphate
tris(2-hydroxyethyl)phosphate
tris(2-mercaptoethyl)phosphate
tris(2-methylthioethyl)phosphate
tris(2-ethoxyethyl)phosphorotrithioate
tris(2-phenoxyethyl)phosphorotrithioate
trifurfuryl phosphorotrithioate
tris(2-mercaptoethyl)phosphorotrithioate
tris(2-aminoethyl)phosphorotrithioate
tris(2-hydroxyethyl)phosphorotrithioate
N,N',N''-tris-(2-ethoxyethyl)phosphorictriamide
hexa(2-hydroxyethyl)phosphorictriamide
hexa(2-ethoxyethyl)phosphorictriamide
hexa(2-tetrahydropyranylmethyl)phosphorictriamide
hexa(2-ethylthioethyl)phosphorictriamide, and
hexa(2-mercaptoethyl)phosphorictriamide, and with a first proviso that said polymeric component is other than a polyurethane, and
with a second proviso that said composition contains about 20 to 30% by weight of filler when said polymeric component is ethylene-propylene rubber or ethylene-propylene-diene monomer copolymer and said composition contains 0 to less than 10% by weight of filler when said polymeric component is other than said rubber or said copolymer.

14. A polymeric composition as in claim 13 in which said polymeric component is crosslinked.

15. A polymeric composition as in claim 14 in which said compound is tris(2-ethoxyethyl)phosphate.

16. A polymeric composition as in claim 14 in which said compound is tris(2-butoxy ethyl)phosphate.

17. A polymeric composition as in claim 14 which is unfilled.

18. A polymeric composition as in claim 17 in which said polymeric component is polyethylene.

19. Power cable insulated with the composition of claim 13.

20. Power cable insulated with the composition of claim 18.

* * * * *